United States Patent [19]
Asai et al.

[11] Patent Number: 4,872,203
[45] Date of Patent: Oct. 3, 1989

[54] IMAGE INPUT DEVICE FOR PROCESSING A FINGERPRINT PRIOR TO IDENTIFICATION

[75] Inventors: Ko Asai; Koichiro Morita, both of Tokyo, Japan

[73] Assignee: NEC Corporation, Tokyo, Japan

[21] Appl. No.: 172,935

[22] Filed: Mar. 25, 1988

Related U.S. Application Data

[63] Continuation of Ser. No. 755,810, Jul. 17, 1985, abandoned.

[30] Foreign Application Priority Data

| Jul. 18, 1984 | [JP] | Japan | 59-148893 |
| Aug. 8, 1984 | [JP] | Japan | 59-166083 |
| Aug. 8, 1984 | [JP] | Japan | 59-166084 |
| Aug. 8, 1984 | [JP] | Japan | 59-166085 |
| Aug. 30, 1984 | [JP] | Japan | 59-181105 |
| Aug. 30, 1984 | [JP] | Japan | 59-181107 |

[51] Int. Cl.$^4$ ............................................. G06K 9/00
[52] U.S. Cl. ........................................ 382/4; 382/30; 382/52
[58] Field of Search ............... 382/4, 5, 30, 61, 37, 382/38, 50, 52; 356/71

[56] References Cited
U.S. PATENT DOCUMENTS

| 3,944,978 | 3/1976 | Jensen et al. | 382/4 |
| 3,947,833 | 3/1976 | Echstein, Jr. | 382/37 |
| 3,975,711 | 8/1976 | McMahon | 382/4 |
| 4,027,284 | 5/1977 | Hoshino et al. | 382/30 |
| 4,030,068 | 6/1977 | Banz | 382/38 |
| 4,047,154 | 9/1977 | Vitols et al. | 382/5 |
| 4,491,964 | 1/1985 | Sanner | 382/50 |

Primary Examiner—Leo H. Boudreau
Assistant Examiner—Joseph Mancuso
Attorney, Agent, or Firm—Foley & Lardner, Schwartz, Jeffery, Schwaab, Mack, Blumenthal & Evans

[57] ABSTRACT

In an image input device for carrying out a preliminary operation prior to identification of an object placed on an input surface. The preliminary operation is for indicating a start time instant of the identification. Responsive to a succession of image signals extracted from the input surface, a timing controller produces partial image signals selected from the image signal succession in correspondence to positions which are unidimensionally or bidimensionally distributed on the input surface. Alternatively, the preliminary operation is for detecting whether the object is true or false. In this event, grey level comparison may be made as regards selected ones of the image signals that are in correspondence to preselected positions of the input surface. Variation of the image signals may be monitored at two different time instants. A false input can be avoided by changing luminous intensities of the image signals with time or by projecting a specific pattern onto the input surface to detect the specific pattern.

11 Claims, 9 Drawing Sheets

IMAGE INPUT DEVICE FOR PROCESSING A FINGERPRINT PRIOR TO IDENTIFICATION

This application is a continuation of application Ser. No. 755,810, filed July 17, 1985, now abandoned.

BACKGROUND OF THE INVENTION

This invention relates to an image input device for use in combination with an identification system which carries out identification of a fingerprint.

An identification system of the type described identifies each person by the use of attributes of fingerprint impressions that are unique for each person and remain unchanged throughout one's life. It has been a recent trend that the identification system is used not only in a criminal investigation but also in a cash dispensing system or a person identifying system of checking entrance and exit to and from an offlimits zone.

In such a cash dispensing system or the like, identification should accurately be carried out in a real time manner. A distinct and clear fingerprint impression must therefore be derived from a fingertip which will be called an object. In addition, a false or forged fingerprint impression might willfully be used in the cash dispensing system. Therefore, such a false fingerprint impression should be distinguished from an impression derived from a true or natural fingerprint.

In U.S. Pat. No. 3,975,711 issued to D. H. MacMahon, an image input device is disclosed which comprises a transparent prism of an isosceles right triangle having a pair of equilateral sides and a hypotenuse. An input plane is defined along the hypotenuse so as to place a fingertip. A parallel light beam illuminates the fingertip on the input plane to provide an image. The image is sent to an optical pickup system to be converted into an image signal on one hand and is visually monitored through an optical system by an observer or operator on the other hand.

With this structure, it is possible to detect whether or not an impression of the fingerprint is adequate. However, the image input device should be supervised by the observer or operator. In other words, automatic supervision is impossible with the image input device.

SUMMARY OF THE INVENTION

It is an object of this invention to provide an image input device which is for use in combination with an identification system carrying out identification of a fingerprint and which is capable of automatically supervising an impression of the fingerprint prior to the identification so as to decide whether or not the impression is proper.

It is another object of this invention to provide an image input device of the type described, wherein a distinct and clear fingerprint impression can be derived from the fingerprint in the form of an image signal.

It is still another object of this invention to provide an image input device of the type described, wherein a false fingerprint can automatically be detected.

An image input device to which this invention is applicable is for use in combination with an identification system for carrying out identification of an object on an input surface. According to this invention, the image input device comprises image extracting means for preliminarily extracting a preliminary image signal from the input surface prior to identification of said object and detecting means responsive to the preliminary image signal for detecting whether or not the identification is to be carried out.

BRIEF DESCRIPTION OF THE INVENTION

DESCRIPTION OF THE PREFERRED EMBODIMENTS

Principles of the Invention

At first, description will be made about principles of the invention for a better understanding thereof. It is well known that a fingerprint has uniqueness and unchangeability and consists of an arrangement of epidermal ridges. Each ridge is an aggregation of exits of sweat glands.

It has been found out that a fingerprint impression becomes variable and dense with time when a fingertip is actually placed on a transparent plate. This means that the fingerprint impression may preferably be extracted when a preselected interval lapses after the fingertip is placed on the transparent plate. Accordingly, a starting instant of time for extraction may be controlled so as to obtain a distinct and clear image of the fingerprint impression.

Moreover, actual placement of the fingertip on the transparent plate gives rise to variation of the image in grey level, as mentioned before. It is therefore possible to detect whether or not the fingertip is true or false by supervising the variation of the image with time.

Embodiments

Referring to FIGS. 1 through 4, an identification system is for use in carrying out identification of a fingerprint and comprises an image input device 30 according to a first embodiment of this invention. The illustrated identification system is assumed to be applied to a cash dispensing system wherein identification codes are assigned to users or persons, respectively. In addition, it is also assumed that fingerprints of the users are registered and stored in a memory device 31 in the form of pattern signals specifying features of the respective fingerprints. The memory device 31 may be a magnetic drum, a magnetic disk, or the like.

When one of the users inputs an assigned one of the identification codes by manipulating a keyboard or push buttons 32, the assigned identification code is sent to an identification processor 35 which is for carrying out identification of each user in a manner to be described below. Responsive to the assigned identification code, the identification processor 35 accesses the memory device 31 to derive one of the pattern signals from the memory device 31 that corresponds to the assigned identification code.

Figure 1:
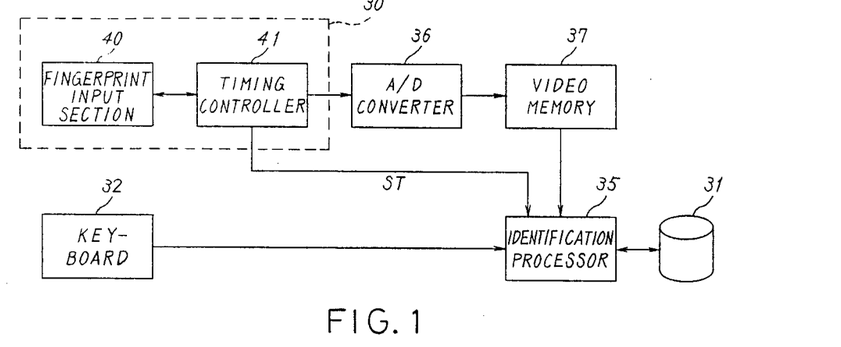
FIG. 1 is a block diagram of an identification system comprising an image input device according to a first embodiment of this invention.

On the other hand, a fingerprint of the user is extracted as a main image signal from the image input device 30 in a manner to be described later and is sent through an analog-to-digital (A/D) converter 36 to a video or image memory 37. As a result, the video memory 37 is loaded with the main image signal representative of the user's fingerprint. The identification processor 35 reads the main image signal out of the video memory 37 and compares the same with the above-mentioned one of the pattern signals read out of the memory device 31. When coincidence is detected between the main image signal and the one pattern signal as a result of comparison, the identification processor 35 completes the identification and makes any other device (not shown) carry out other operations necessary for the cash dispensing system to accept a request of the user. Detection of noncoincidence brings about rejection of the user's request.

In order to accurately carry out the above-mentioned identification, the user's fingerprint should be distinct and clear. Otherwise, accuracy of the identification can not be assured. For this purpose, preliminary operation is carried out by the use of the image input device 30 prior to the identification although the image input device 30 is used on the identification also.

Figure 2:
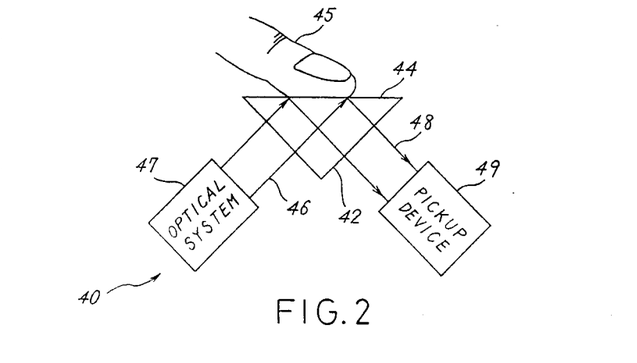
FIG. 2 is a schematic view of a fingerprint input section included in the image input device illustrated in FIG. 1.

In FIG. 1, the image input device 30 comprises a fingerprint input section 40 and a timing controller 41. As shown in FIG. 2, the fingerprint input section 40 comprises a prism 42 of a right-angled isosceles triangle in section. The triangle has equilateral sides directed downwards of FIG. 2 and a hypotenuse directed upwards thereof. An input surface 44 is defined along the hypotenuse while incident and exit surfaces are defined along the equilateral sides, respectively, as will presently become clear.

Figure 3:
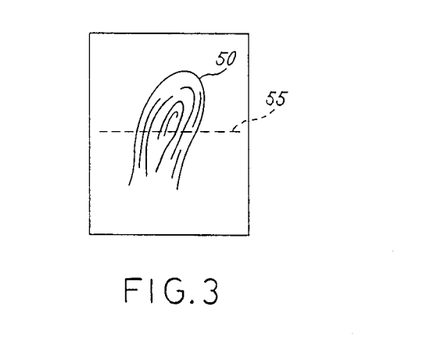
FIG. 3 is a view for use in describing operation of the image input device illustrated in FIG. 1.

The user brings his fingertip 45 into contact with the input surface 44 as the object. Incident light 46 is incident onto the input surface 44 from an optical system 47 comprising a light source and a lens system and is reflected by the input surface 44. Reflected light 48 exits through the exit surface to an industrial television camera, namely, image pickup device 49. The reflected light 48 is subjected to optical modulation on the input surface 44 by the fingertip 45 and therefore forms, on the image pickup device 49, an optical image as illustrated in FIG. 3. Thus, a fingerprint impression 50 appears in the optical image when the fingertip 45 is brought into contact with the input surface 44.

As mentioned before, the fingerprint impression becomes dense with time. Therefore, it is preferable that extraction of the fingerprint impression is carried out after the impression becomes dense. Under the circumstances, a start time instant of the extraction is controlled by the use of the timing controller 41.

Figure 4:
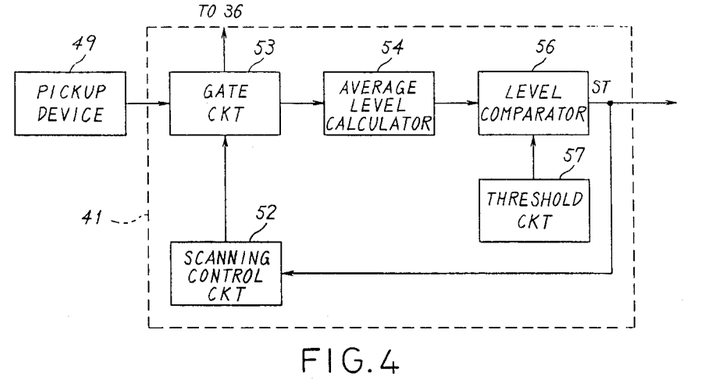
FIG. 4 partially shows a block diagram of an image input device according to a second embodiment of this invention.

More particularly, the optical image is successively picked up by the pickup device 49 and converted into a succession of analog image signals. The analog image signals are sent from the pickup device 49 to the timing controller 41. In FIG. 4, the timing controller 41 comprises a scanning control circuit 52 and a gate circuit 53 controlled by the scanning control circuit 52. During the preliminary operation, the scanning control circuit 52 periodically produces a gate signal for selecting predetermined horizontal scanning line or lines that unidimensionally appear at a center portion of the optical image, as depicted at 55 in FIG. 3. As a result, the gate circuit 53 is enabled for a time interval of the predetermined scanning line or lines to produce a selected image signal succession.

The selected image signal succession is representative of a part of the optical image as illustrated in FIG. 3 and may be called a partial image signal. Thus, a combination of the scanning control circuit 52 and the gate circuit 53 is operable to produce the partial image signal and will be called a partial image signal circuit. The partial image signal appears before the identification of the fingertip 45 and will also be named a preliminary image signal.

Alternatively, the partial image signal can be produced by periodically driving the pickup device 49 by the scanning control circuit 52. In this event, a combination of the pickup device 49 and the scanning control circuit 52 may be referred to as the partial image signal circuit.

Responsive to the partial image signal, an average level calculator 54 calculates an average level of the partial image signal to produce an average signal representative of the average level. The average signal is sent to a level comparator 56 supplied with a threshold level from a threshold circuit 57. The level comparator 56 compares the average level with the threshold level to produce an extraction start signal ST when the average level is higher than the threshold level. The extraction start signal ST is delivered to the identification processor 35 (FIG. 1) to start the identification of the fingerprint impression. On the other hand, the identification is not carried out while the extraction start signal ST is not produced.

Thus, the average level calculator 54, the level comparator 56, and the threshold circuit 57 serve to detect whether or not the identification is to be carried out.

Supplied with the extraction start signal ST, the scanning control circuit 52 continuously enables the gate circuit 36. Consequently, the analog image signal is delivered as a main image signal to the analog-to-digital converter 36 (FIG. 1) and processed for the identification in the manner mentioned above.

Figure 5:
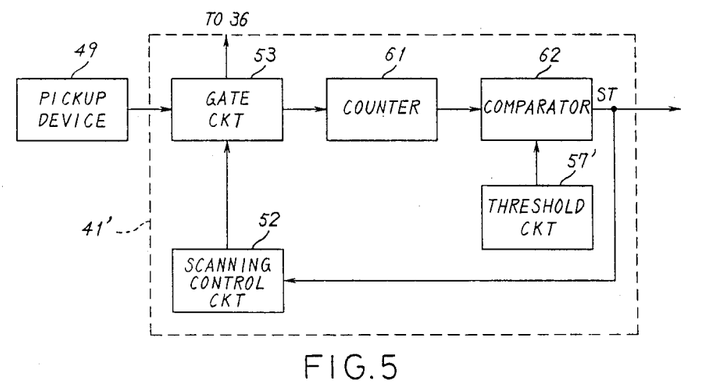
FIG. 5 is a similar view of a modification of the image input device illustrated in FIG. 4.

Referring to FIG. 5 together with FIGS. 1 and 2, an image input device 30 according to a modification of the first embodiment comprises a timing controller 41' which is similar to that illustrated in FIG. 4 except that the partial image signal produced from the gate circuit 53 is processed in a digital manner. To this end, the illustrated timing controller 41' comprises a counter 61, a comparator 62, and a threshold circuit 57'. Specifically, the fingerprint impression as illustrated in FIG. 3 comprises a plurality of ridges and a plurality of valleys interposed between two adjacent ones of the ridges. The ridges and the valleys can be represented by high and low levels of the optical image, respectively, in the manner known in the art and are therefore converted into high and low levels of the analog image signals, respectively. The counter 61 counts the number of the ridges by monitoring the analog image signals. The number of the ridges is compared in the comparator 62 with a threshold value given from the threshold circuit 57'. In this event, the counter 61 detects whether or not the partial image signal takes the high level at every picture element lined up along the horizontal scanning line or lines and produces a succession of pulses on detection of the high level of the partial image signal. Thereafter, the pulse is successively counted to provide the number of ridges.

Like in FIG. 4, the extraction start signal ST is produced when the number of the ridges is greater than the threshold value.

In FIG. 5, the counter 61 should rapidly be operated in synchronism with each picture element lined up along the predetermined horizontal line or lines. Such a rapid operation of the counter 61 might make accurate detection of the extraction start instant difficult because of a short interval of the predetermined horizontal line or lines.

Figure 6:
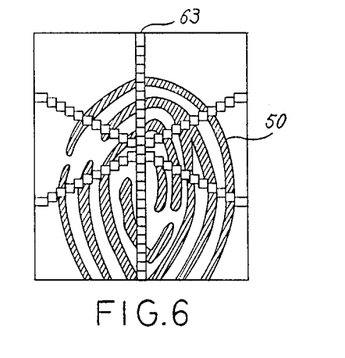
FIG. 6 is a view for use in describing operation of an image input device according to a second embodiment of this invention.
Figure 7:
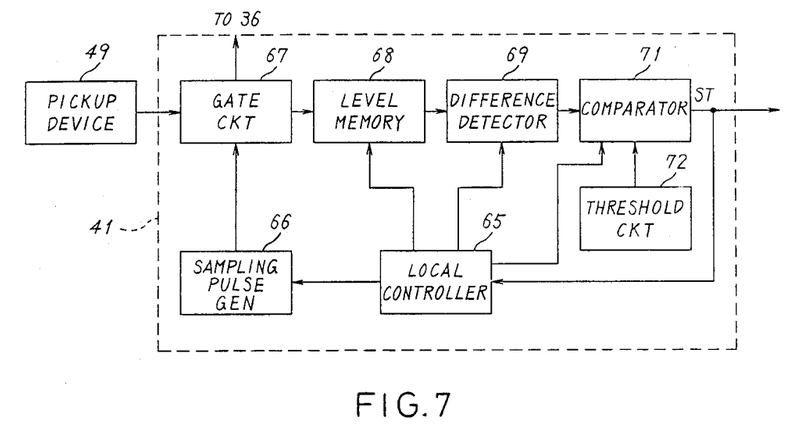
FIG. 7 is a block diagram of the image input device according to the second embodiment of this invention.

Referring to FIGS. 6 and 7 together with FIGS. 1 and 2, an image input device 30 according to a second embodiment of this invention is for use in sampling the optical image so as to accurately detect the extraction start instant. In FIG. 6, the fingerprint impression 50 is radially sampled on the optical image at sampling positions depicted at 63. As readily understood from FIG. 6, the sampling positions 63 correspond to sampling instants at which the analog image signal is sampled. Each of the sampling instants is separated from adjacent sampling instants. Accordingly, sampling is made about the picture elements which are remote from one another in comparison with the picture elements lined up along a horizontal scanning line. Inasmuch as the fingerprint impression becomes dense with time, remote sampling of the picture elements enables accurate detection of the fingerprint impression.

In order to carry out the above-mentioned sampling, the image input device comprises a timing controller 41 illustrated in FIG. 7. More particularly, the timing controller 41 comprises a local controller 65 for indicating the picture elements placed at the sampling positions 63 shown in FIG. 6. For this purpose, the local controller 65 supplies a sampling pulse generator 66 with a succession of timing pulses indicative of the sampling positions 63. The timing pulse succession is delivered to a gate circuit 67 as sampling pulses The gate circuit 67 is enabled only when each of the sampling pulses is present. Consequently, the analog image signal is sampled or gated at the sampling instants in correspondence to the sampling positions 63 to be sent as sampled picture elements to a level memory 68. The sampled picture elements may be of a digital form. At any rate, the sampled picture elements are representative of a part of the fingerprint impression and will be called the partial image signal.

The sampled picture elements are stored under control of the local controller 65 in those addresses of the level memory 68 which are predetermined for the sampling positions 63, respectively. When all of the sampled picture elements are stored in the level memory 68, two adjacent ones of the sampled picture elements are successively read out of the level memory 68 and sent to a difference detector 69 for successively detecting level differences between the two adjacent ones of the sampled picture elements. The difference detector 69 successively sums up the level differences to produce a sum signal representative of a sum when the level differences are calculated as regards all of the sampled picture elements. The sum signal is supplied to a comparator which is depicted at 71 and which is given a threshold level from a threshold circuit indicated at 72. The comparator 71 compares the sum with the threshold level to produce an extraction start signal ST in the manner described in conjunction with FIGS. 4 and 5. The extraction start signal ST is also delivered to the local controller 65. The local controller 65 continuously enables the gate circuit 67 through the sampling pulse generator 66 to make the gate circuit 67 supply the analog image signal to the analog-to-digital converter 36 (FIG. 1).

Thus, the preliminary operation is finished and proceeds to the identification of the fingerprint impression.

Figure 8:
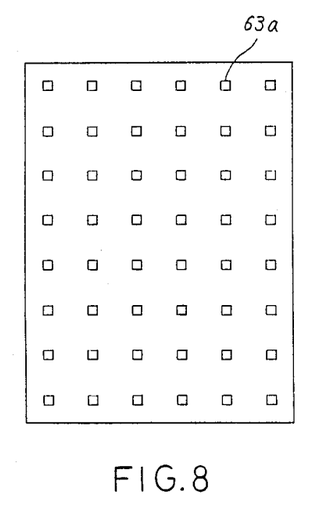
FIG. 8 is a view for use in describing an example of operation similar to that illustrated in FIG. 6.

Referring to FIG. 8, sampling positions 63a are regularly arranged on the optical image to sample or select picture elements appearing at a constant interval of time. In this event, the local controller 65 (FIG. 7) may periodically deliver the timing pulses to the sampling pulse generator 66 at the constant interval. Stated otherwise, the local controller 65 may memorize the constant interval and therefore becomes simple in structure.

Figure 9:
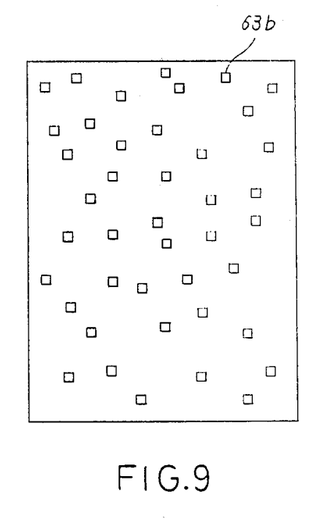
FIG. 9 is a similar view for use in describing another example of operation.

Referring to FIG. 9, another example of a sampling position arrangement has sampling positions 63b irregularly distributed or scattered on the optical image. With this example, the sampling positions can be determined by random numbers to sample or select the picture elements thereat.

It is to be noted here that the fingerprint has a ridge arrangement comprising a lot of curved ridges arranged in order. An irregular distribution of the sampling positions 63b serves to uniformly select the ridges and the remaining portions. Uniform detection of the fingerprint impression is therefore possible all over the optical image.

Figure 10:
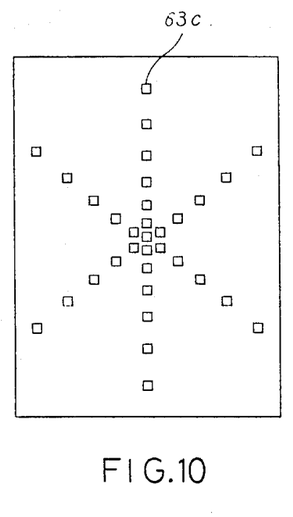
FIG. 10 is a similar view for use in describing still another example of operation.
Figure 11:
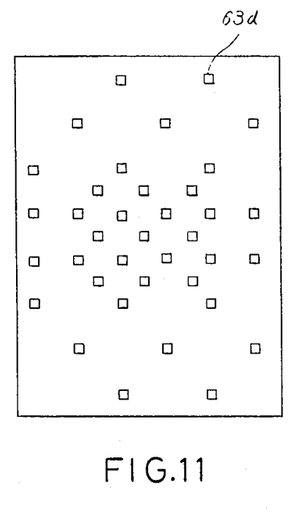
FIG. 11 is a similar view for use in describing yet another example of operation.
Figure 12:
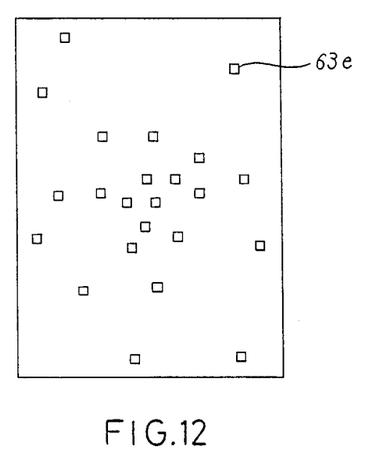
FIG. 12 is a similar view for use in describing another example of operation.

Referring to FIGS. 10 through 12, sampling positions 63c, 63d, and 63e are distributed on the optical images, respectively. In FIG. 10, the sampling positions 63c are radially and discretely arranged from a center portion of the optical image to a peripheral portion surrounding the center portion. In FIGS. 11 and 12, the sampling positions 63d and 63e are irregularly arranged. In any event, each distribution of the sampling positions 63c to 63e is dense or thick at the center portion and is rough or thin at the peripheral portion. The sampling positions 63a to 63e are bidimensionally distributed on the optical images, namely, the input surface.

With this structure, it becomes difficult to detect the fingerprint impression which is placed at the peripheral portion. In other words, the fingerprint impression is readily detected when it is placed at the center portion. This means that an indication is audibly or visually made about changing a position of the fingerprint impression when the impression is present at the peripheral portion. Such an indication can be made in a well known manner.

Now, it is possible to accurately and artificially reproduce or print a fingerprint on a medium, such as a plastic film, a rubber sheet, or the like. Such an artificial medium and its fingerprint may be called a false object and an artificial fingerprint, respectively. In this connection, a human's fingertip and its fingerprint may be called a true object and a natural fingerprint, respectively.

In addition, it is known in the art that the artificial medium, such as the plastic film, can closely be adhered to a glass surface when liquid, such as water, is interposed between the plastic film and the glass surface. In this event, the artificial medium might wrongly be identified in the above-exemplified identification systems. This might bring about unfavorable things.

Figure 13:
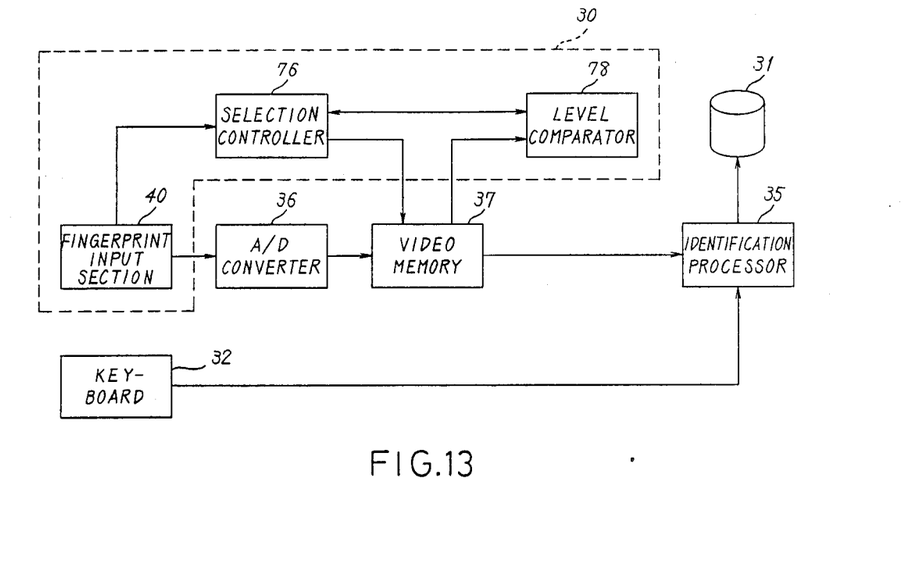
FIG. 13 is a block diagram of an identification system comprising an image input device according to a third embodiment of this invention.
Figure 14:
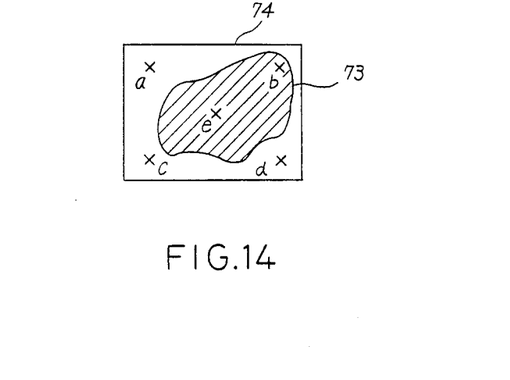
FIG. 14 is a view for use in describing operation of the image input device illustrated in FIG. 13.
Figure 15:
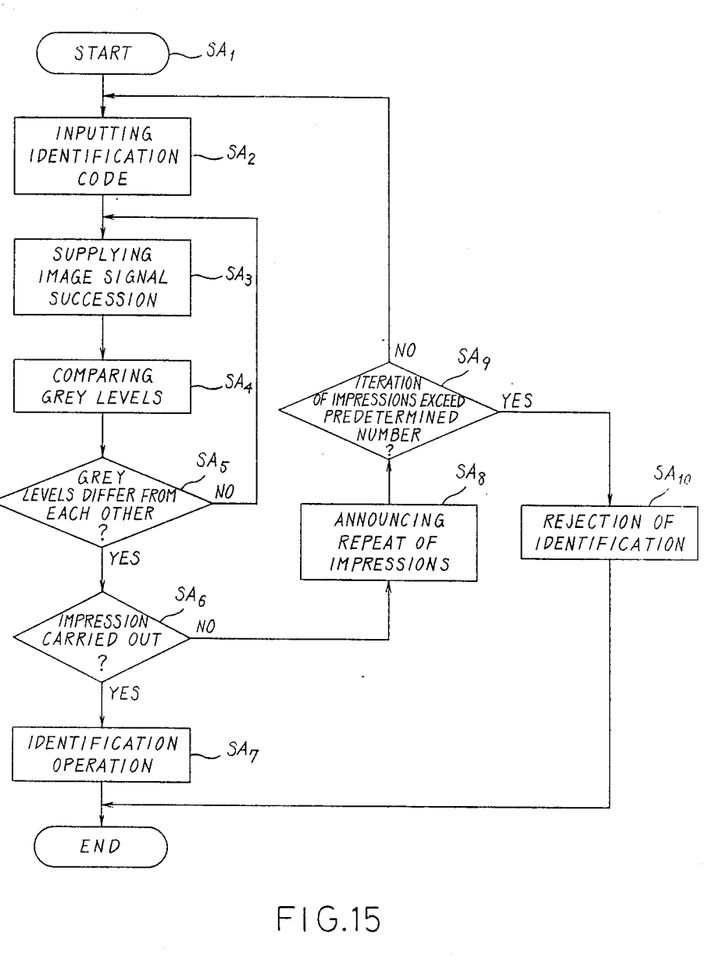
FIG. 15 is a flow chart for use in describing operation of the identification system illustrated in FIG. 13.

Referring to FIGS. 13 through 15, an identification system illustrated in FIG. 13 is for use in distinguishing between the true and the false objects and comprises an image input device according to a third embodiment of this invention.

Let the false object be placed on the input surface with liquid interposed between the false object and the input surface. In this event, a shade 73 partially appears due to presence of liquid on an optical image 74 derived from the false object, as illustrated in FIG. 14. If the liquid is uniform in thickness on the whole of the input surface, the optical image might be kept uniform in grey level. However, it is difficult to rapidly form a uniform liquid layer on the whole of the input surface. Accordingly, the shade 73 inevitably occurs on the optical image.

Therefore, the presence of the liquid can be detected by monitoring a variation of grey levels of picture elements at a plurality of selected positions, such as a through e of the optical image. In the sample being illustrated, the identification system carries out the preliminary operation so as to detect the presence or absence of liquid.

More specifically, in reference to FIG. 15 the preliminary operation is started at a first step SA$_1$ followed by a second step SA$_2$ at which an assigned identification code is supplied from the keyboard 32 to the identification processor 35.

Subsequently, the analog image signal succession is successively supplied from the fingerprint input section 40 through the analog-to-digital converter 36 to the video memory 37 as a succession of digital image signals, as shown at a third step SA$_3$ in FIG. 15. Such supply of the analog image signals is supervised by a selection controller 76 included in the image input device 30. Thus, the digital image signals for one frame are stored in the video memory 37. Thereafter, the selection controller 76 selects the picture elements corresponding to the selected positions a to e. The selected picture elements are delivered to a level comparator 78 and may be called the preliminary image signal.

At a fourth step SA$_4$, the level detector 78 compares grey levels of two of the selected picture elements with each other. At a fifth step SA$_5$, the selection controller 76 detects whether or not a difference of the grey levels between the two picture elements is greater than a preselected level. Let the difference be greater than the preselected level. This implies that something is located on the input surface. Therefore, the fifth step SA$_5$ is succeeded by a sixth step SA$_6$ at which the selection controller 76 detects whether the impression is the true or the false impression. Such detection is carried out in the manner described in conjunction with FIG. 14. More specifically, a ratio of grey levels of the picture elements is low when the fingerprint is normally impressed on the input surface and is high on presence of the shade 73 (FIG. 14). Therefore, the judgement is possible by comparing the ratio of grey levels with a threshold value.

On detection of the normal impression, the identification of the fingerprint is carried out at a seventh step SA$_7$ in the manner described in conjunction with FIG. 1.

On no detection of the normal impression, the sixth step SA$_6$ is followed by an eighth step SA$_8$ at which an announcement is audibly or visually made about iteration of the fingerprint impression in a known manner. At a ninth step SA$_9$, the selection controller 76 counts the iteration of the fingerprint impressions and judges whether or not the iteration of the fingerprint impressions exceeds a predetermined number of times. If the iteration exceeds the predetermined number, the ninth step SA$_9$ is succeeded by a tenth step SA$_{10}$ at which the identification is rejected. Otherwise, the ninth step SA$_9$ is followed by the second step SA$_2$ at which the identification code is inputted by the use of the keyboard 32.

The selection controller 76 may be a single-chip processor known in the art.

Figure 16:
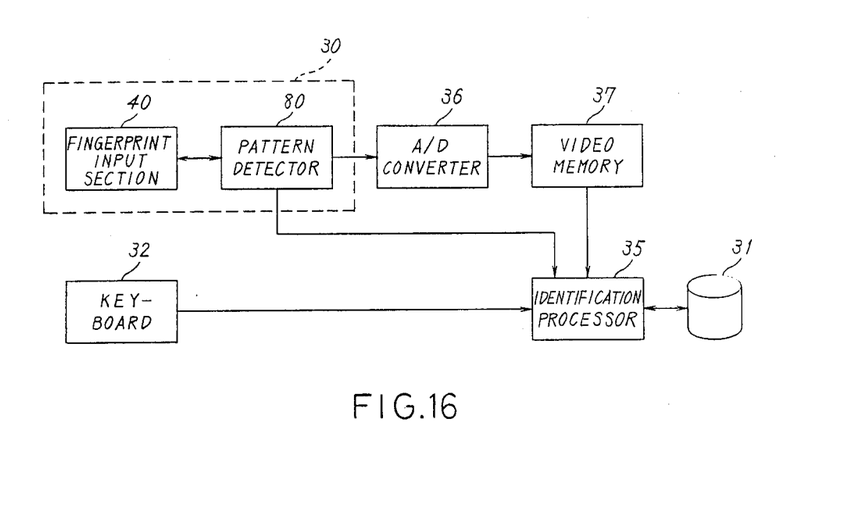
FIG. 16 is a block diagram of an identification system comprising an image input device according to a fourth embodiment of this invention.

Referring to FIG. 16, an identification system is for use in detecting whether an object is true or false and is similar in structure to that illustrated in FIG. 1 except that the identification system (FIG. 13) comprises an image input device 30 according to a fourth embodiment of this invention so as to carry out the above-mentioned detection of the object even when the shade 73 (FIG. 14) is uniformly formed on the input surface.

More specifically, the image input device 30 illustrated in FIG. 13 comprises a fingerprint input section 40 similar to that illustrated in FIG. 2 and a pattern detector 80 for detecting either the true object or the false one prior to the identification of a fingerprint. As a result, the identification is carried out only for the true object.

It is mentioned before that a fingerprint impression of a human's fingertip becomes dense with time. This is because the human's fingertip inevitably causes sweat to occur on the input surface 44 (FIG. 2) due to hidrosis or sweating and reflection of the incident light is dependent on an amount of the sweat. On the other hand, no variation takes place as regards a fingerprint impression resulting from the false object.

Figure 17:
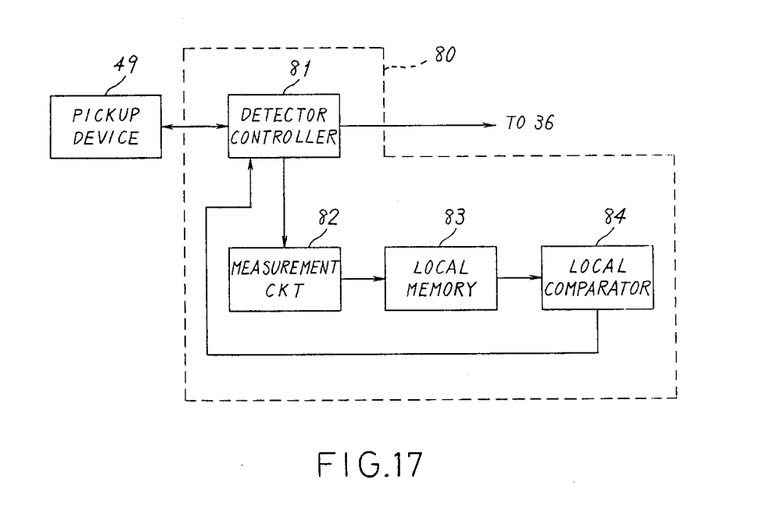
FIG. 17 is a block diagram of an image input device according to a fifth embodiment of this invention.
Figure 18:
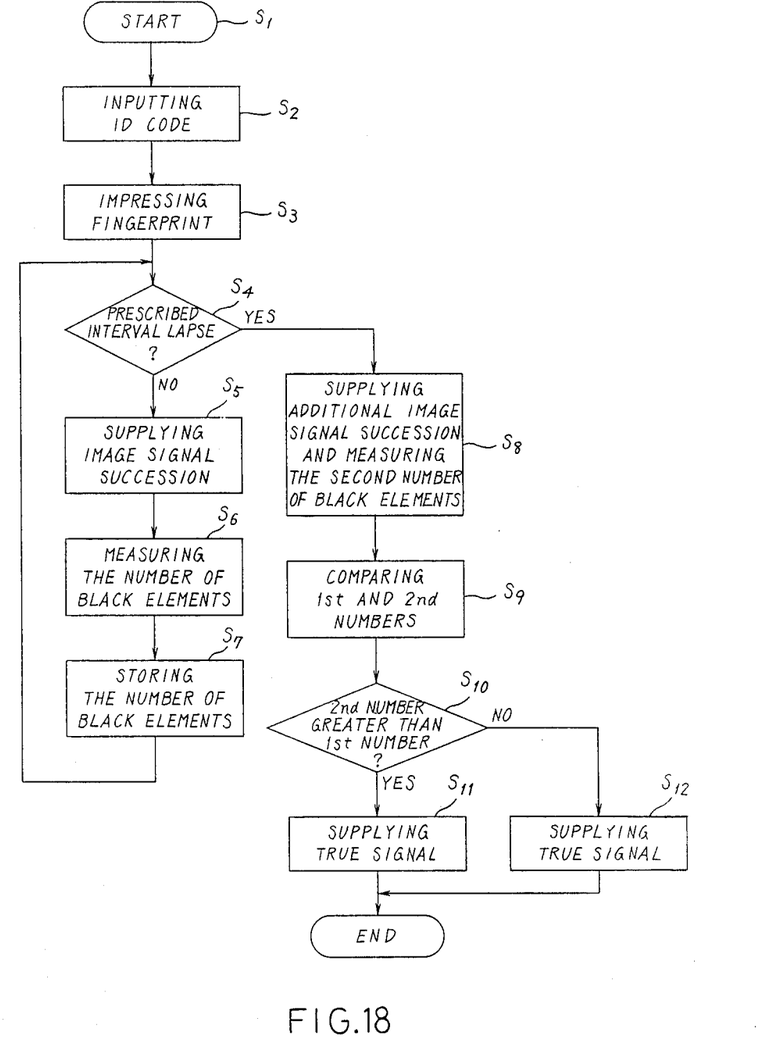
FIG. 18 is a flow chart for use in describing operation of the image input device illustrated in FIG. 17.

Referring to FIGS. 17 and 18 together with FIG. 16, the pattern detector 80 illustrated in FIG. 17 carries out the above detecting operation in consideration of a variation of the fingerprint impression. The detecting operation is started as the preliminary operation at a first step S$_1$ in FIG. 18. Each person inputs an assigned identification code at a second step S$_2$ by manipulating the keyboard 32 (FIG. 16) and places one's fingertip on the input surface 44 (FIG. 2) of the fingerprint input section 40 at a third step S$_3$.

During the detecting operation, the analog image signal succession is sent to a detector controller 81. At a fourth step $S_4$, the detector controller 81 monitors whether or not a prescribed interval of time lapses. The prescribed interval may be several seconds or so and will become clear as the description proceeds. When the prescribed interval does not yet lapse, the fourth step $S_4$ is followed by a fifth step $S_5$.

At the fifth step $S_5$, the detector controller 81 is supplied from the pickup device 49 with a first succession of the analog image signals each of which has a variable grey level and which is produced at a first time instant. The first analog image signal succession may last for one frame and is delivered from the detector controller 81 to a measurement circuit 82 (FIG. 17). The measurement circuit 82 detects whether or not each analog image signal is a black picture element and thereafter measures the number of the black picture elements as a first number, as shown at a sixth step $S_6$. The first number is representative of a result of measurement. The first number of the black picture elements is stored in a local memory 83 (FIG. 17) at a seventh step $S_7$.

The seventh step $S_7$ proceeds to the fourth step $S_4$ at which lapse of the prescribed interval is monitored by the detector controller 81. When the prescribed interval lapses, the fourth step $S_4$ is succeeded by an eighth step $S_8$ at which an additional or second succession of the analog image signals is sent through the detector controller 81 to the measurement circuit 82. The additional succession is derived at a second time instant at which the prescribed interval lapses after the first time interval. The number of black picture elements is measured as a second number as regards the additional succession by the measurement circuit 82 and stored in the local memory 83.

Anyway, the first and the second successions are delivered as the preliminary image signal to the measurement circuit 82.

At a ninth step $S_9$, the second number of black picture elements is compared by a local comparator 84 with the first number of black picture elements. The local comparator 84 judges at a tenth step $S_{10}$ whether or not the second number is greater than the first number. When the second number is greater than the first number, the local comparator 84 supplies the detector controller 81 with a true signal indicative of detection of the true object at an eleventh step $S_{11}$. Otherwise, the local comparator 84 produces a false signal indicative of detection of the false object at a twelfth step $S_{12}$.

After production of either the true signal or the false signal, the detecting operation is finished and followed by the identification. Therefore, each of the true and the false signals may be called the preliminary signal.

It is noted here that the artificial fingerprint can maliciously be inputted through an additional optical system (not shown) different from the normal optical system 47 illustrated in FIG. 2. It is preferable to avoid such a malicious input of the artificial fingerprint.

Figure 19:
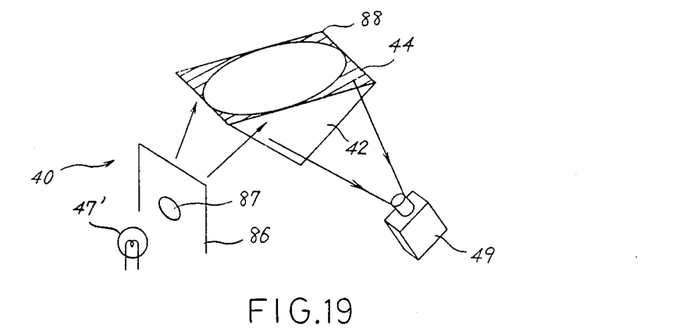
FIG. 19 is a schematic view of an image input device according to a sixth embodiment of this invention.
Figure 20:
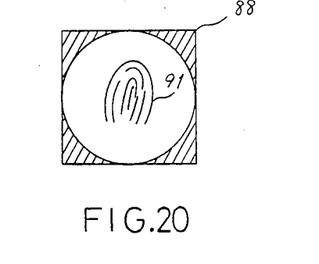
FIG. 20 is a view for use in describing operation of the image input device illustrated in FIG. 19.

Referring to FIGS. 19 and 20, an image input device according to a sixth embodiment of this invention comprises a fingerprint input portion 40 comprising a shutter plate 86 between a prism 42 similar to that illustrated in FIG. 2 and a light source 47'. The shutter plate 86 has a circular window 87 and is illuminated by the incident light emitted from the light source 47'. As a result, the incident light is projected onto the input surface 44 through the circular window 87 and is partially intercepted by the shutter plate 86. Therefore, a shading pattern 88 appears along a periphery of the input surface 44, as shown in FIG. 19 to define a circular center area of the input surface 44 inside the shading pattern 88. The shading pattern 88 is picked up by the pickup device 49 together with a fingerprint impression depicted at 91 in FIG. 20.

It is readily possible to detect such a shading pattern 88 in a known manner by a pattern detector 80 as described in conjunction with FIG. 16. The shading pattern 88 and the impression 91 are picked up by the pickup device 49 to be produced as the preliminary image signal. Responsive to the preliminary image signal, the pattern detector 80 may regard presence or absence of the shading pattern 88 as the true object or the false one, respectively.

The window 87 may not be circular but of an optional geometric configuration, such as a rectangle, a pentagon, or the like. The shutter 86 may be altered if it is stolen.

Figure 21:
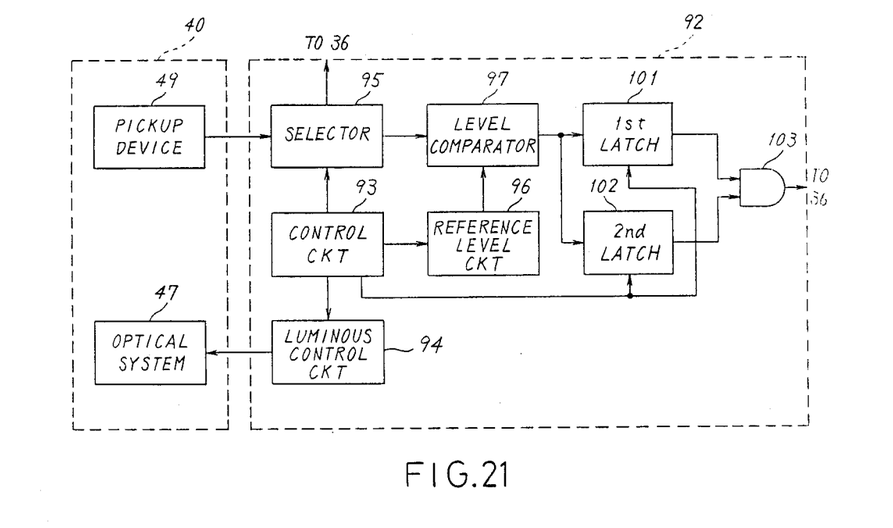
FIG. 21 is a block diagram of an image input device according to a seventh embodiment of this invention.

Referring to FIG. 21, an image input device according to a seventh embodiment of this invention comprises a luminous intensity controller 92 coupled to a fingerprint input section 40 similar to that illustrated in FIG. 2. The luminous intensity controller 92 is operable to control a luminous intensity of the optical system 47 in order to distinguish between a normal input and a malicious input carried out through the optical system 47 and the additional optical system (not shown), respectively.

More specifically, let a fingertip be placed on the input surface 44 (FIG. 1) and an optical image be picked up from the input surface by the use of the optical system 47. In this event, the optical image includes a fingerprint image and a background image surrounding the fingerprint. The background image is kept constant in luminous intensity as long as the input surface is illuminated by the incident light of a first constant luminous intensity. It is assumed that the background image is sampled at a plurality of background positions which may be adjacent to four corners of the optical image.

The luminous intensity controller 92 comprises a control circuit 93 for controlling circuit elements included in the luminous intensity controller 92, as will become clear as the description proceeds. The control circuit 93 at first puts a luminous control circuit 94 into operation. Consequently, the optical system 47 illuminates the input surface 44 (FIG. 2) with a first luminous intensity under control of the luminous control circuit 94.

First analog image signals are picked up by the pickup device 49 and sent to a selector 95 of the luminous intensity controller 92. The control circuit 93 supplies the selector 95 with a succession of selection signals appearing at time instants corresponding to the background positions. Accordingly, the first analog image signals are sampled at first sampled image signals at the time instants corresponding to the background positions. Thus, the first sampled image signals are representative of the background image and are representative of signal levels. The first sampled image signals may be called the preliminary image signal.

On the other hand, the control circuit 93 delivers a first level control signal to a reference level circuit 96. Responsive to the first level control signal, the reference level circuit 96 supplies a level comparator 97 with a first reference level corresponding to the first constant luminous intensity.

The level comparator 97 successively compares each signal level of the first sampled image signals with the first reference level to produce a first succession of result signals representative of results of comparison. The first succession is delivered to a first latch 101 under control of the control circuit 93.

After the first succession of result signals is stored in the first latch 101, the control circuit 93 controls the luminous control circuit 94. Consequently, the incident light of a second luminous intensity is emitted from the optical system. The pickup device 49 picks up the optical image again to produce second analog image signals.

The second analog image signals are selected by the selector 95 as second sampled image signals sampled at the background positions. The second sampled image signals may also be called the preliminary image signal. In this event, the reference level circuit 96 is supplied with a second level control signal to produce a second reference level which is different from the first reference level and which is selected in consideration of the second constant luminous intensity. The level comparator 97 compares each signal level of the second sampled image signals with the second reference level to produce a second succession of result signals representative of results of comparison. The second succession of result singals is sent to a second latch 102 to be kept therein under control of the control circuit 93.

If the optical system 47 is used in combination with the luminous intensity controller 92, the first succession has to coincide with the second succession. In other words, use of the additional optical system results in noncoincidence between the first and the second successions.

Taking the above into consideration, the first and the second successions are supplied to an AND circuit 103 in parallel to produce a detection signal representative of either the coincidence or the noncoincidence. When the detection signal is representative of the coincidnece, the identification is carried out in the manner described before. Otherwise, no identification is carried out. The detection signal serves as the preliminary signal produced prior to the identification.

Thus, the malicious input is favorably rejected by the use of the illustrated image input device 30.

While this invention has thus far been described in conjunction with several embodiments thereof, it will readily be possible for those skilled in the art to put this invention into practice in various other manners. For example, the fingerprint input section 40 may comprise an analog-to-digital converter for converting the analog image signals into digital image signals In this case, the image input device 30 processes the digital image signals. It is readily possible to construct various controllers, such as 52, 65, and the like, in a manner known in the art.

What is claimed is:

1. An image input device for use in pre-processing a fingerprint impressed on an input surface to determine, before said fingerprint is identified by means of an identification unit, whether or not said identification of the fingerprint is to be started, said device comprising:

signal producing means for producing an optical image signal representative of an optical image of said fingerprint which is impressed on said input surface and which varies in density with time;

timing control means responsive to said optical image signal for controlling a time interval of selecting said optical image signal to produce a partial image signal representative of a part of said optical image at a predetermined position of said input surface; and detecting means responsive to said partial image signal for detecting density of said partial image so as to determine whether or not an extraction start signal is produced, said extraction start signal allowing supply of said optical image signal to said identification unit.

2. An image input device as claimed in claim 1, wherein said timing control means comprising:

gate signal producing means for periodically producing a gate signal within the time interval during which a predetermined part of said optical image signal is produced by the signal producing means, said predetermined part of the optical image signal being representative of said part of the optical image at the predetermined position; and gate means responsive to said optical image signal and said gate signal for gating said optical image signal within said time interval to produce said predetermined part of the optical image signal as said partial image signal.

3. An image input device as claimed in claim 1, wherein said detecting means comprises:

average level calculating means coupled to said timing control means for calculating an average level of said partial image signal to produce an average level signal representative of said average level; and deciding means coupled to said average level calculating means and responsive to said average level signal for deciding whether or not said extraction start signal is produced.

4. An image input device as claimed in claim 1, wherein said partial lamp signal carries a plurality of picture elements and assumes high and low levels synchronized with said picture elements, and wherein said detecting means comprises:

counting means responsive to said partial image signal for counting either one of said high and said low levels in synchronism with said picture elements to produce a count signal representative of the count; and deciding means coupled to said counting means and responsive to said count signal for deciding whether or not said extraction start signal is produced.

5. An image input device as claimed in claim 1, wherein said timing control means comprises:

sampling pulse producing means for producing a succession of sampling pulses at every one of sampling instants which define said time interval; and gating means responsive to said sampling pulses for gating said optical image signal to produce said partial image signal at said sampling instants.

6. An image input device as claimed in claim 1, wherein said time interval is made to correspond to a center portion of said input surface which is defined as said predetermined position.

7. An image input device as claimed in claim 1, wherein said time interval is made to correspond to parts of said input surface which are bidirectionally distributed on said input surface and which are defined as said predetermined position.

8. An image input device as claimed in claim 7, wherein said parts are radially arranged on said input surface.

9. An image input device as claimed in claim 7, wherein said parts are regularly distributed on said input surface.

10. An image input device as claimed in claim 7, wherein said parts are irregularly distributed on said input surface.

11. An image input device as claimed in claim 7, wherein said parts are more densely distributed at a center portion of said input surface and less densely distributed at a peripheral portion surrounding said center portion.

* * * * *